United States Patent [19]

Reinhardt et al.

[11] 4,380,619
[45] Apr. 19, 1983

[54] OXY- AND THIOARYL-PHENYLATED AROMATIC HETEROCYCLIC POLYMERS

[75] Inventors: Bruce A. Reinhardt, New Carlisle; Fred E. Arnold, Centerville, both of Ohio

[73] Assignee: The United States of America as represented by the Secretary of the Air Force, Washington, D.C.

[21] Appl. No.: 366,744

[22] Filed: Apr. 8, 1982

[51] Int. Cl.$^3$ ............... C08G 2/26; C08G 12/00
[52] U.S. Cl. ................... 526/259; 526/285; 528/125; 528/128; 528/172; 528/183; 528/184; 528/185; 528/205; 528/206; 528/208; 528/226; 528/228; 528/229
[58] Field of Search ............... 526/259, 285; 528/125, 528/128, 172, 183, 184, 185, 228, 226, 229, 205, 206, 208

[56] References Cited

U.S. PATENT DOCUMENTS

| | | | |
|---|---|---|---|
| 3,905,941 | 9/1975 | Jones | 526/259 |
| 3,975,363 | 8/1976 | Jones | 526/259 |
| 4,108,835 | 8/1978 | Arnold et al. | 528/183 |
| 4,147,858 | 4/1979 | Evers | 526/259 |
| 4,268,654 | 5/1981 | Arnold et al. | 526/259 |

*Primary Examiner*—Lester L. Lee
*Attorney, Agent, or Firm*—Donald J. Singer; Charles E. Bricker

[57] ABSTRACT

Oxy- and thio-aryl-phenylated aromatic heterocyclic polymers having the general formula

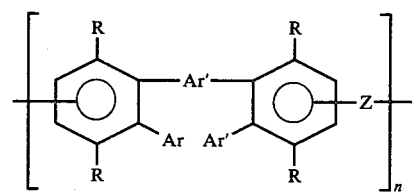

wherein Ar is a monovalent aromatic radical containing an oxy- or thio-linkage, Ar′ is a divalent aromatic radical, R is a monovalent aromatic radical, Z is a divalent heterocyclic radical and n is an integer equal to the number of repeating units, are prepared from biscyclopentadienones with diethynyl heterocyclic compounds.

13 Claims, No Drawings

OXY- AND THIOARYL-PHENYLATED AROMATIC HETEROCYCLIC POLYMERS

RIGHTS OF THE GOVERNMENT

The invention described herein may be manufactured and used by or for the Government of the United States for all governmental purposes without the payment of any royalty.

BACKGROUND OF THE INVENTION

This invention relates to aromatic heterocyclic polymers.

High temperature resins presently available have various drawbacks which limit their use in many applications. A serious one frequently encountered is the evolution of volatiles during the curing cycle, which makes it imperative that the entire curing cycle be carried out under pressure. For example, polyimides when cured release volatile components which cause gas bubble or void formation in the cured resin unless considerable pressure is maintained during the curing operation in order to prevent these undesirable results. When phenolic resins are cured, water is released which also causes void formation unless the curing reaction is carried out under pressure.

Acetylene-terminated compounds show promise for use in the preparation of matrix resins and adhesives for advanced aircraft and aerospace systems, and for other high-temperature applications. These compounds can be polymerized thermally without the evolution of volatile by-products, thereby obviating the problem of void formation in composite structures and molded articles.

Although many of the aromatic, heterocyclic, and aromatic/heterocyclic polymers exhibit superior mechanical and thermal properties, many of these polymers exhibit the disadvantages that they are soluble only in polar solvents, generally strong acids, which is a disadvantage from a processing standpoint.

It is therefore an object of the present invention to provide polymer systems having improved solubility characteristics.

It is another object of the invention to provide polymer systems which exhibit the desired superior physical properties as well as the required high degree of thermal stability.

Other objects and advantages of the invention will be apparent to those skilled in the art upon consideration of the following disclosure.

DESCRIPTION OF THE INVENTION

In accordance with the present invention there is provided a heterocyclic polymer of the general formula

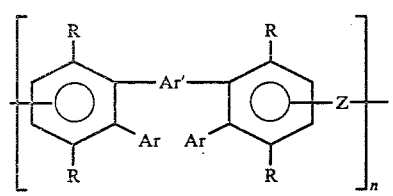

wherein Ar is a monovalent aromatic radical containing an oxy or thio linkage, Ar' is a divalent aromatic radical, R is a monovalent aromatic radical, Z is a divalent heterocyclic radical and n is an integer equal to the number of repeating units. In general, the number of repeating units is such that the polymer has an intrinsic viscosity of about 0.25 to 0.75 dl/g as determined in dimethylacetamide at 30° C.

Examples of monovalent aromatic radicals Ar include the following:

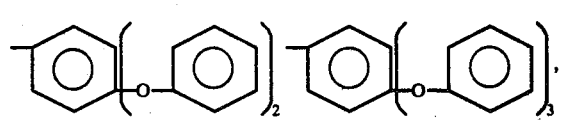

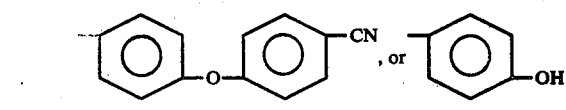

Examples of divalent aromatic radicals Ar' include the following:

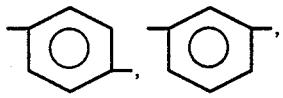

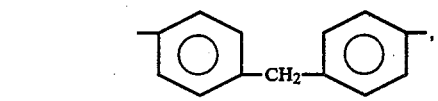

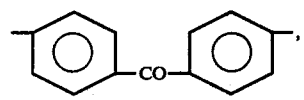

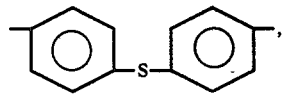

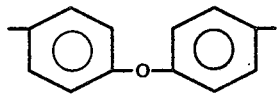

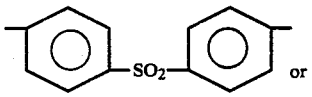

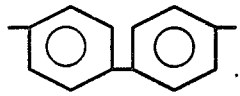

The following are examples of the heterocyclic radical Z:

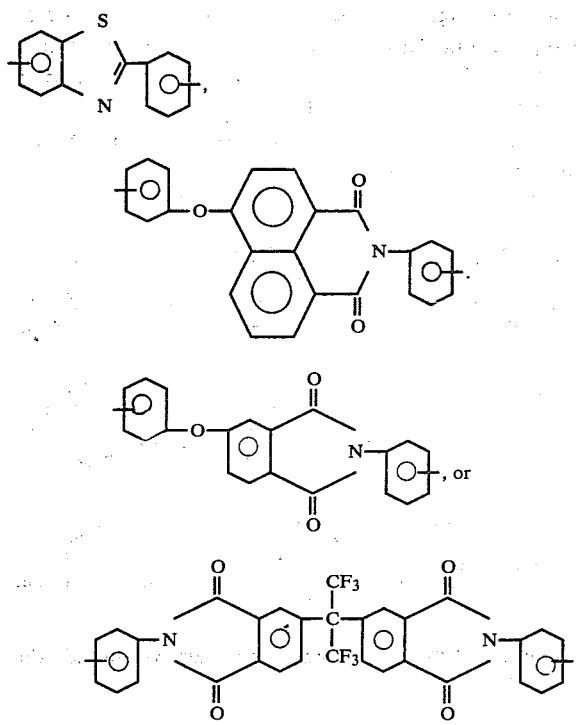

The monovalent aromatic radical R may be

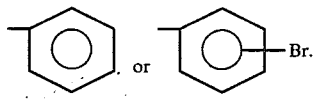

The polymers I are prepared by the reaction of a biscyclopentadienone compound with a diethynyl heterocyclic compound. The reaction may be represented by the following equation:

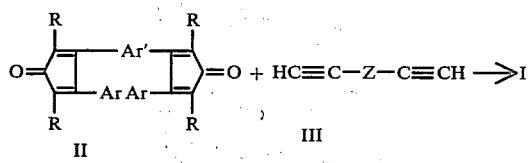

wherein R, Ar, Ar' and Z are as defined previously.

As shown by the above equation, substantially equimolar amounts of the biscyclopentadienone compound and the diethynyl heterocyclic compound are utilized. This reaction is carried out in the presence of a suitable solvent, one which is inert to the reactants and the resulting polymer, and one in which at least the monomers are soluble. Examples of suitable solvents include 1,2,4-trichlorobenzene, sym-tetrachloroethane, sulfolane, isopropylbenzene, o-dichlorobenzene, xylene, and the like. The temperature at which the reaction is carried out usually ranges from about 100° to 250° C. Generally, the reaction period ranges from about 20 to 100 hours, although longer and shorter periods can be used.

At the end of the reaction period, the polymer is recovered by a general procedure that is conventionally followed in solution polymerization processes. For example, the reaction mixture is poured into a non-solvent for the polymer, e.g., an alcohol such as methanol, thereby causing the polymer to precipitate from solution. The precipitated polymer is then separated from solution by any suitable means, such as by filtration or decantation. The separated polymer may thereafter be washed with an alcohol. If desired, the polymer can be redissolved in a solvent and again precipitated from solution by pouring the solution into an alcohol. This procedure can be repeated as necessary to further purify the product.

The biscyclodienone monomer II is prepared by the reaction of an aromatic bis-benzil with a benzylketone. The reaction involved is represented by the following equation:

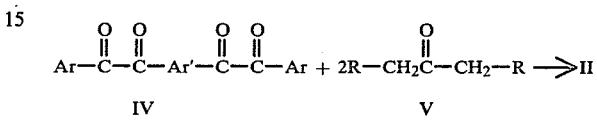

The terms Ar, Ar' and R are as defined previously.

As shown by the above equation, an aromatic bis-benzil is reacted with a 1,3-bis aromatic-2-propanone to form a biscyclopentadienone II. The compounds IV and V are generally employed in a ratio of about 1:2, respectively, although the ketone V may be employed in an amount up to about 50% excess, if desired. The reaction is carried out in the presence of an alkali metal hydroxide under reflux conditions in a suitable reaction medium. An alcohol, such as ethanol, can be conveniently used as the reaction medium. The amount of alkali metal hydroxide can vary within rather broad limits, but generally ranges from about 0.1 to 0.75 mole per mole of the aromatic bis-benzil. The reaction medium is usually maintained under reflux conditions for a period ranging from 15 minutes to 1 hour. The bis-dienone product II may be recovered from the reaction mixture by conventional procedures, such as by filtration. It may, if desired, be further purified by chromatography.

The aromatic bis-benzils of Formula IV are well known compounds that are described in the literature. Examples of such compounds include:

m-bis(p'-methoxyphenylglyoxylyl)benzene,
m-bis(p'-phenoxyphenylglyoxylyl)benzene,
m-bis[p'-(p''-phenoxy)phenoxyphenylglyoxylyl]benzene,
m-bis[p'-(p''-[p'''-phenoxy]phenoxy)phenoxyphenylglyoxylyl]benzene,
m-bis[p'-(p''-cyano)phenoxyphenylglyoxylyl]benzene, and
m-bis(p'-hydroxyphenylglyosylyl)benzene.

The benzyl ketone V may be 1,3-bisphenyl-2-propanone or a halogenated derivative thereof, such as 1,3-bis(p-bromophenyl)-2-propanone.

The heterocyclic monomer III having the formula

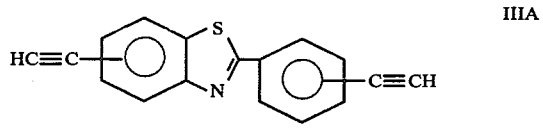

is a new compound and is disclosed and described in application Ser. No. 356,576 filed by one of us as coinventor on Mar. 9, 1982. Examples of compounds of the above formula are 2-(4-ethynylphenyl)-5-ethynylbenzothiazole, 2-(3-ethynylphenyl)-5-ethynylbenzothiazole, 2-(4-ethynylphenyl)-6-ethynylbenzothiazole, and 2-(3-ethynylphenyl)-6-ethynylbenzothiazole.

The heterocyclic monomer III having the formula

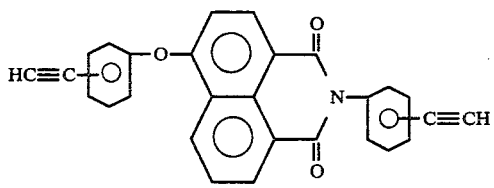 IIIB may be prepared as shown by the following equations:

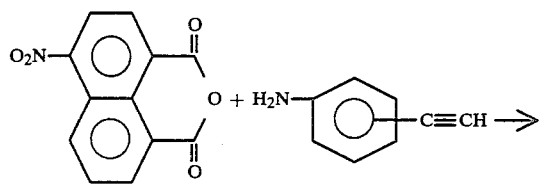

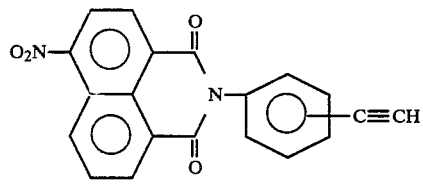

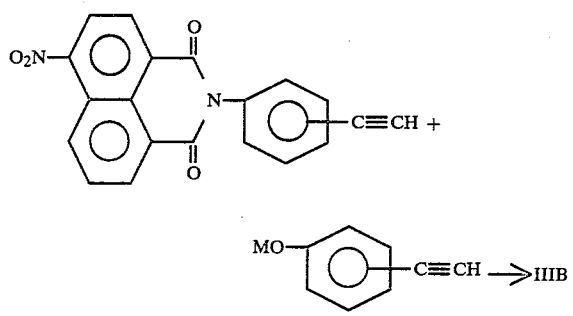

wherein the symbol M indicates an alkali metal.

As shown by the above equations, 4-nitro naphthalic anhydride is first reacted with an aminophenylacetylene. The resulting monoethynylphanylimide is then reacted with an alkali metal salt of an ethynylphenol to form the heterocyclic monomer IIIB.

The condensation reaction is conducted under an inert atmosphere, such as nitrogen, argon, helium, or the like. The reaction may be conveniently carried out in acetic acid under reflux conditions for about 1 to 2 hours. The intermediate product may be recovered by filtration.

The diethynyl heterocyclic monomer IIIB is prepared by reacting the condensation product with an alkali metal salt of an ethynylphenol. This alkali metal salt may be conveniently prepared from, for example, sodium methoxide and 3- or 4-ethynylphenol. Preparation of the diethynyl heterocyclic monomer IIIB is carried out under an inert atmosphere, in an aprotic solvent at a temperature of about 60°–80° C. for about 1–2 hours. Suitable aprotic solvents include, N,N-dimethylacetamide, N,N-diethylacetamide, N,N-dimethylformamide, N,N-diethylformamide, N-methyl-2-pyrrolidone, tetramethyl urea, hexamethylphosphoramide, sulfolane and the like. The reaction mixture is cooled, then poured into ice water. Generally, the product IIIB will precipitate out when the mixture is poured into the ice water. If the precipitate fails to form, the ice water mixture may be acidified to promote precipitation. The precipitate is then collected by filtration. The product may be further purified by chromatography.

The heretocyclic monomer III having the formula

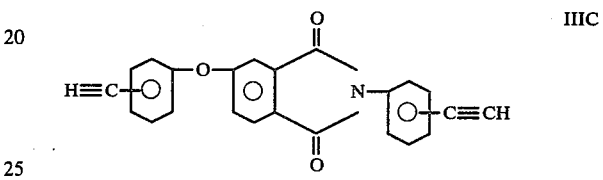 IIIC may be prepared using a procedure similar to that described above for preparing the monomer IIIB.

The heterocyclic monomer III having the formula:

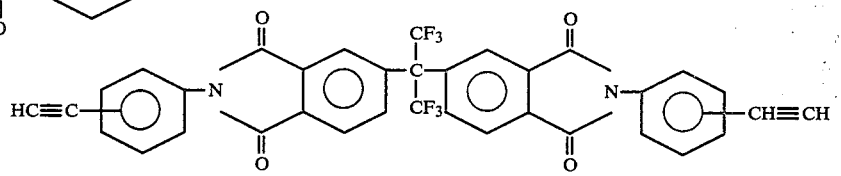

may be prepared by the condensation of 2,2-bis(3',4'-dicarboxyphenyl)hexafluoropropane dianhydride with 3- or 4-ethynylaniline. This condensation reaction is carried out in a manner similar to the condensation reaction described previously.

The polymers I are soluble in a variety of low-boiling, nonacidic solvents. Examples of suitable solvents include chloroform, benzene, toluene, 1,2,4-trichlorobenzene, and the like.

The following examples illustrate the invention.

EXAMPLE I

Preparation of
2-(4-Ethynylphenyl)-5-ethynylbenzothiazole

A mixture of 20 g (0.083 mole) of 4-bromo-2-aminothiophenol hydrochloride and 270 g of deoxygenated polyphosphoric acid was heated at 70° C. for 4 hours. To this mixture was added a solution containing 22 g (0.11 mole) of p-bromobenzoic acid dissolved in 109 g of sulfolane. The reaction mixture was slowly heated to 200° C. and maintained at that temperature for 1 hour. After cooling, the reaction mixture was poured into a 1:1 water-methanol solution to precipitate the product. The light tan precipitate was filtered, washed with dilute ammonium hydroxide, washed with water, and then air dried. The 2-(4-bromophenyl)-5-bromobenzothiazole was recrystallized from toluene to give 24.5 g (80% of theoretical), m.p. 162°–163° C.

Analysis: Calc'd for $C_{13}H_7NSBr$: C,42.30; H,1.90; N,3.90; Found: C,42.2; H,1.56; N,3.81

A mixture of 28 g (0.078 mole) of 2-(4-bromophenyl)-5-bromobenzothiazole, 0.09 g of triphenylphosphine palladium II dichloride, 0.7 g of triphenylphosphine, 0.26 g of cuprous iodide and 250 ml of triethylamine was degassed by passing nitrogen through the system for 20 minutes. To the degassed mixture was added 28 g (0.33 mole) of 2-methyl-3-butyne-2-ol. The reaction mixture was heated to 90° C. and maintained at that temperature for 24 hours. After cooling, the precipitated amine hydrobromide was removed by filtration. The filtrate was evaporated under reduced pressure leaving a brown solid. The solid was then dissolved in chloroform. The chloroform solution was washed with a 10% sulfuric acid solution, then with water, and thereafter dried over anhydrous magnesium sulfate. The chloroform was removed under reduced pressure, yielding 27 g (100% of theoretical) of the bisbutynol adduct which was used without purification.

A mixture of 27 g (0.078 mole) of the bis-butynol adduct dissolved in 250 ml of toluene and 2.0 g of powdered potassium hydroxide was heated to reflux. The progress of the reaction was monitored by thin layer chromatography. After about 4 hours, all the starting material was hydrolyzed. The reaction mixture was filtered and the toluene was removed under reduced pressure. The residue was eluted through a silica gel column using methylene chloride as the eluant. Removal of the eluant provided 18.4 g (91% of theoretical) of pure product: m.p. 150°–161° C.

Analysis Calc'd for $C_{17}H_9SN$: C,78.74; H,3.50; N,5.40; S12.36; Found: C,78.43; H,2.91; N,5.07; S,12.03

EXAMPLE II

Preparation of N-3-Ethynylphenyl-4-(3-ethynylphenoxy)naphthalimide

A mixture of 24.3 g (0.10 mole) of 4-nitronaphthalic anhydride and 11.7 g (0.10 mole) of 3-aminophenyl-acetylene in 300 ml of glacial acetic acid was refluxed under nitrogen for 1 hour, then cooled and filtered. The precipitate was washed with methanol and air dried. Recrystallization from toluene gave 20.0 g (58% yield) of N-3-ethynylphenyl-4-nitronaphthalimide, m.p. 265°–267° C. (decomposes).

Analysis Calc'd for $C_{20}H_{10}N_2O_4$: C,70.17; H,2.94; N,8.18; Found: C,69.85; H,2.73; N,8.41

To the sodium salt of 3-ethynylphenol, prepared from 5.95 g (0.05 mole) of 3-ethynylphenol and 2.7 g (0.05 mole) of sodium methoxide in methanol and benzene and dried by distillation with additional benzene, under nitrogen, was added 200 ml of dry N,N-dimethylacetamide. The mixture was heated to 70° C., then 17.1 g (0.05 mole) of N-3-ethynylphenyl-4-nitronaphthalimide was added. The resulting dark solution was heated at 70° C. for 1 hour, then cooled and poured into 2.5 liters of ice water. The precipitate was collected by filtration and air dried. Chromatography of the solid air dried silica gel using methylene chloride as the eluant gave 7.5 g (36% yield) of product, m.p. 200°–202° C.

Analysis Calc'd for $C_{28}H_{15}NO_3$: C,81.34; H,3.65; N,38; Found: C,81.45; H,3.67; N,3.42

EXAMPLE III

Preparation of 4-(3-Ethynylphenoxy)-N-(3-ethynylphenyl)phthalimide

To a solution of 10.7 g (0.10 mole) of 4-nitrophthalic anhydride in 150 ml of glacial acetic acid was added 12.9 g (0.11 mole) of 3-ethynylaniline. A white precipitate formed immediately. The mixture was heated to reflux for 1 hour, then cooled and filtered. The precipitate was washed with water and methanol. Recrystallization from toluene gave 25.7 g (87% yield) of 4-nitro-N-(3-ethynylphenyl)phthalimide, m.p. 257°–259° C.

Analysis Calc'd for $C_{16}H_3N_2O_4$: C,65.75; H,2.75; N,9.58; Found: C,65.25; H,2.45; N,9.84.

To the sodium salt of 3-ethynylphenol, prepared from 4.3 g (0.037 mole) of sodium methoxide was added 50 ml of dry N,N-dimethylacetamide, under nitrogen. The mixture was heated to 70° C. and 12.0 g (0.041 mole) of 4-nitro-N-(3-ethynylphenyl)-phthalimide was added. The dark mixture was stirred at 70° C. for 3 hours, then poured into 1.5 liters of ice water. About 100 ml of 1 N sulfuric acid was added to the cold mixture to precipitate the product. The precipitate was collected by filtration, air dried, dissolved in 100 ml of methylene chloride, than again filtered. Chromotography of the filtrate on silica gel using 1:1 hexane:methylene chloride as the eluent gave 5.8 g (44% yield) of product, m.p. 150°–160° C.

Analysis Calc'd for $C_{24}H_{13}NO_3$: C,79.33; H,3.60; N,3.85; Found: C,79.12; H,3.45; N,3.98.

EXAMPLE IV

Preparation of 3,3'-(1,3-phenylene)bis(2,5-diphenyl-4-p-phenoxyphenyl cyclopentadienone)

A stirred suspension of 10 g (19 mmol) of m-bis(p'-phenoxyphenylglyoxylyl)benzene and 8.4 g (40 mmol) of 1,3-diphenylacetone in 250 ml of 95% ethanol was heated to reflux. To this mixture was added 20 ml of 0.53 N KOH in 2 portions over a period of 5 minutes. The reaction mixture changed color to purple immediately upon addition of the first portion of KOH. Heating was continued for 40 minutes, during which time a purple precipitate formed. The crude product was purified by chromatography on a dry silica gel column using toluene as the eluent. 15.2 recovered (82.7% yield) m.p. 205°–206° C.

Analysis Calc'd for $C_{64}H_{42}O_4$: C,87.85; H,4.84; Found: C,87.50; H,5.10

EXAMPLE V

Preparation of 3,3'-(1,3-phenylene)bis(2,5-diphenyl-4-p-thiophenoxyphenyl cyclopentadienone)

A solution of 10 g (17.9 mmol) of m-bis(p'-thiophenoxyphenylglyoxylyl)benzene and 10.5 g (50 mmol) of 1,3-diphenylacetone in 225 ml of 95% ethanol was heated to reflux. To the reaction mixture was added 25 ml of 0.53 N KOH. Upon addition of the KOH, the solution changed color to brown. Heating was continued for 30 minutes. The reaction mixture was allowed to cool to room temperature, then filtered and air dried, providing 16.0 g (98.8% yield) of crude product. This crude product was purified by column chromatography using dry silica gel and toluene as the eluent. The purified product melted at 246°–248° C.

Analysis Calc'd for C_{64}H_{42}S_2O_2: C,84.73; H,4.66; Found: C,84.57; H,4.42

EXAMPLE VI

Polymer Preparation

A mixture of 3.368 g (3.85 mmol) of 3,3'-(1,3-phenylene)bis(2,5-diphenyl-4-p-phenoxyphenyl cyclopentadienone) and 1.0 g (3.85 mmol) of 2-(3-ethynylphenyl-5-ethynylbenzothiazole (m.p. 169° C.) was placed in a 20 ml polymerization tube with 7 ml of sym-tetrachloroethane. The contents of the tube were degassed by several freeze-thaw cycles at liquid nitrogen temperature, then sealed in vacuo. The sealed polymerization tube was placed in a Parr Bomb pressure reactor and heated to 225° C. for 42 hours. The tube was cooled to room temperature. After opening, 8 ml of chloroform was added to the viscous solution in the tube. The take contents were poured into methanol to precipitate out the polymer, which was recovered by filtration, yielding 4.0 g (96% of theoretical). The polymer exhibited an intrinsic viscosity of 0.30 as determined in N,N-dimethylacetamide at 30° C. Other properties of the polymer are shown in Table I below.

Analysis Calc'd for C_{79}H_{51}NSO_2: C,87.99; H,4.77; Found: C,87.70; H,4.58

EXAMPLE VII

A series of heterocyclic polymers were prepared following generally the procedure given in Example VI. The physical properties of these polymers are set forth in Table I below. In the table, the symbols X and Z have reference to the following specific structure;

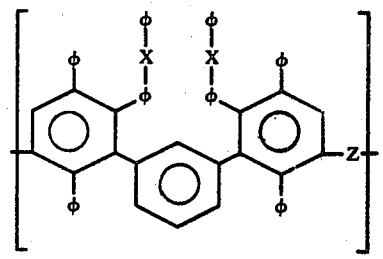

wherein the symbol -φ represents a phenyl group, -φ- represents a p-phenylene group, and X is O or S. In the table, Tg indicates the glass transition temperature, as determined by DSC at a rate of 10° C./minute. The entry "Isothermal Aging, %", indicates the weight percent retained following thermal aging in air at 650° F. for 200 hours.

TABLE I

| X | Z | [η] | Tg, °C. | Isothermal Aging, % |
|---|---|---|---|---|
| O | (benzothiazole structure A) | 0.30 | 282 | 50 |
| S | " | 0.35 | 255 | 80 |
| O | (benzothiazole structure B) | 0.45 | 269 | 55 |
| S | " | 0.28 | 266 | 35 |
| O | (phthalimide-phenoxy-phenyl structure) | 0.61 | 238 | 80 |
| S | " | 0.30 | 233 | 89 |
| O | (naphthalimide-phenoxy-phenyl structure) | 0.54 | 273 | 44 |
| S | " | 0.26 | 264 | 29 |

TABLE I-continued

| X | Z | [n] | Tg, °C. | Isothermal Aging, % |
|---|---|---|---|---|
| O | 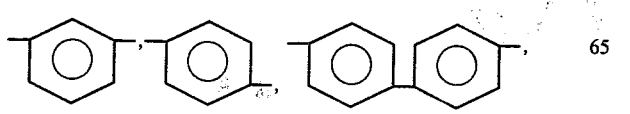 | 0.55 | 240 | 86 |

Various modifications of the present invention can be made in view of the foregoing disclosure without departing from the spirit and scope of the invention.

We claim:

1. A polymer consisting essentially of recurring units having the following formula:

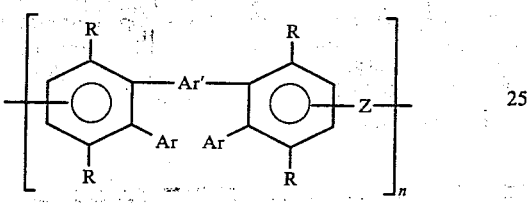

wherein Ar is a monovalent aromatic group containing an oxy or thio linkage, Ar' is a divalent aromatic group, R is a monovalent aromatic group, and Z is a divalent heterocyclic radical selected from the group consisting of

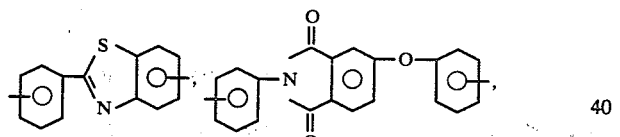

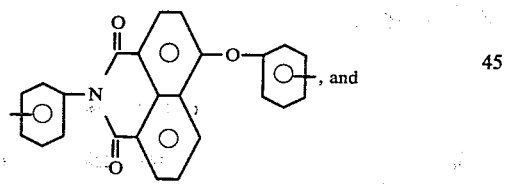, and

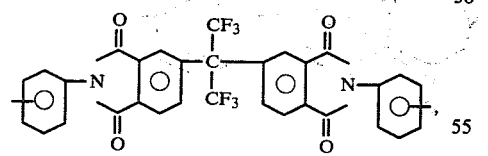, and wherein n is an integer having a value such that the polymer has an intrinsic viscosity in the approximate range of 0.25 to 0.75 as measured in N,N-dimethylacetamide at 30° C.

2. The polymer of claim 1 wherein Ar' is

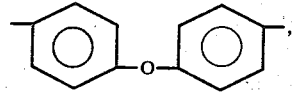

-continued

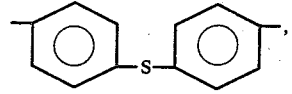

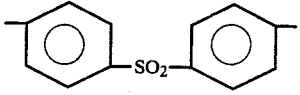

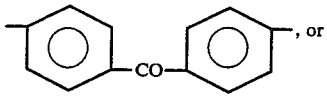

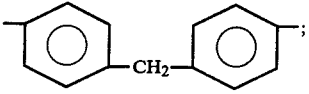, or

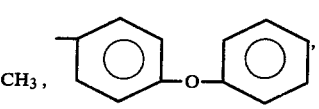;

Ar is

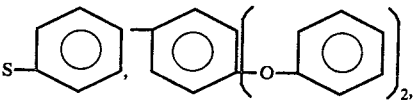

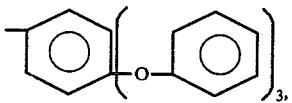

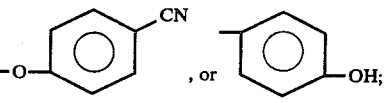, or —OH;

and R is 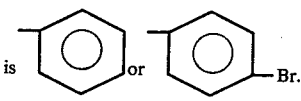

3. The polymer of claim 2 wherein Z is

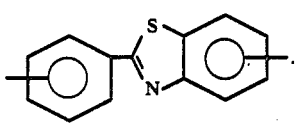

4. The polymer of claim 2 wherein Z is

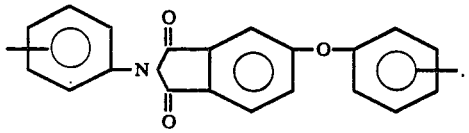

5. The polymer of claim 2 wherein Z is

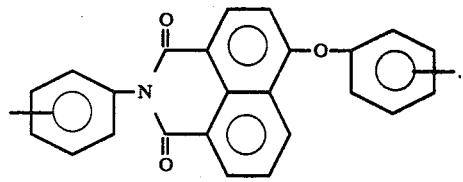

6. The polymer of claim 2 wherein Z is

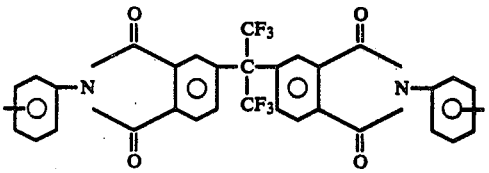

7. The polymer of claim 3 wherein each R is -phenyl, Ar' is m-phenylene and each Ar is p-thiophenoxyphenyl.

8. The polymer of claim 3 wherein each R is -phenyl, Ar' is m-phenylene and each Ar is p-phenoxyphenyl.

9. The polymer of claim 4 wherein each R is -phenyl, Ar' is m-phenylene and each Ar is p-thiophenoxyphenyl.

10. The polymer of claim 4 wherein each R is -phenyl, Ar' is m-phenylene and each Ar is p-phenoxyphenyl.

11. The polymer of claim 5 wherein each R is -phenyl, Ar' is m-phenylene and each Ar is p-thiophenoxyphenyl.

12. The polymer of claim 5 wherein each R is -phenyl, Ar' is m-phenylene and each Ar is p-phenoxyphenyl.

13. The polymer of claim 6 wherein each R is -phenyl, Ar' is m-phenylene and each Ar is p-phenoxyphenyl.

* * * * *